(12) United States Patent
Shao et al.

(10) Patent No.: US 10,125,175 B2
(45) Date of Patent: Nov. 13, 2018

(54) METHOD FOR ENHANCING IMMUNOGENICITY OF EPITOPE PEPTIDE OF HPV ANTIGEN, VIRUS-LIKE PARTICLE, AND METHOD FOR PREPARING HPV VACCINE

(71) Applicant: CANSINO BIOLOGICS INC., Tianjin (CN)

(72) Inventors: Zhongqi Shao, Tianjin (CN); Junqiang Li, Tianjin (CN); Rong Jiang, Tianjin (CN); Mingming Yang, Tianjin (CN); Tao Zhu, Tianjin (CN); Helen Huihua Mao, Tianjin (CN); Xuefeng Yu, Tianjin (CN)

(73) Assignee: CANSINO BIOLOGICS INC., Tianjin (CN)

( * ) Notice: Subject to any disclaimer, the term of this patent is extended or adjusted under 35 U.S.C. 154(b) by 0 days.

(21) Appl. No.: 15/438,790

(22) Filed: Feb. 22, 2017

(65) Prior Publication Data

US 2017/0166612 A1    Jun. 15, 2017

Related U.S. Application Data

(63) Continuation-in-part of application No. PCT/CN2015/086636, filed on Aug. 11, 2015.

(30) Foreign Application Priority Data

Aug. 22, 2014    (CN) .......................... 2014 1 0419379

(51) Int. Cl.
| | | |
|---|---|---|
| *C07K 14/025* | (2006.01) | |
| *A61K 39/29* | (2006.01) | |
| *C12N 15/66* | (2006.01) | |
| *A61K 39/12* | (2006.01) | |
| *C12N 7/04* | (2006.01) | |
| *A61K 39/00* | (2006.01) | |

(52) U.S. Cl.
CPC ............ *C07K 14/025* (2013.01); *A61K 39/12* (2013.01); *C12N 7/04* (2013.01); *C12N 15/66* (2013.01); *A61K 2039/5258* (2013.01); *A61K 2039/575* (2013.01); *A61K 2039/6075* (2013.01); *C07K 2319/00* (2013.01); *C12N 2710/20034* (2013.01)

(58) Field of Classification Search
None
See application file for complete search history.

(56) References Cited

PUBLICATIONS

Tindle et al. Chimeric Hepatitis B Core Antigen Particles Containing B- and Th-Epitopes of Human Papillomavirus Type 16 E7 Protein Induce Specific Antibody and T-Helper Responses in Immunised Mice. Virology, 1994, 200:547-557.*
Jagu S, Kwak K, Karanam B, Huh WK, Damotharan V, et al. (2013) Optimization of Multimeric Human Papillomavirus L2 Vaccines. PLoS ONE 8(1): e55538.*
GenBank: AFN85007.1. L2 protein [Human papillomavirus type 16]. Dated Jul. 28, 2012.*

* cited by examiner

*Primary Examiner* — Nianxiang Zou
(74) *Attorney, Agent, or Firm* — Raymond Y. Chan; David and Raymond Patent Firm (57) ABSTRACT

A method for enhancing immunogenicity of an epitope peptide of an HPV antigen, the method including: assembling a gene of an HPV antigen into a gene of HBc, exogenously expressing a resulting assembled gene to acquire a fusion protein, allowing the fusion protein to automatically assemble to form a virus-like particle including the HPV antigen on a surface of the virus-like particle, to obtain HBc-HPV virus-like particle. A virus-like particle capable of expressing the antigen peptide of HPV acquired by the method. The virus-like particle includes a HBc-L2 fusion protein. A genome for encoding the HBc-L2 fusion protein is represented by SEQ ID NO. 3. A method for preparing an HPV vaccine includes using the virus-like particle.

4 Claims, 7 Drawing Sheets

Specification includes a Sequence Listing.

FIG. 9

SEQUENCE LISTING

```
<160> NUMBER OF SEQ ID NOS: 5

<210> SEQ ID NO 1
<211> LENGTH: 35
<212> TYPE: PRT
<213> ORGANISM: Human papillomavirus

<400> SEQUENCE: 1

Ala Ser Ala Thr Gln Leu Tyr Lys Thr Cys Lys Gln Ala Gly Thr Cys
1               5                   10                  15
```

Pro Pro Asp Ile Ile Pro Lys Val Glu Gly Lys Thr Ile Ala Asp Gln
            20                  25                  30

Ile Leu Gln
        35

<210> SEQ ID NO 2
<211> LENGTH: 17
<212> TYPE: PRT
<213> ORGANISM: Human papillomavirus

<400> SEQUENCE: 2

Gly Thr Gly Gly Arg Thr Gly Tyr Ile Pro Leu Gly Thr Arg Pro Pro
1               5                   10                  15

Thr

<210> SEQ ID NO 3
<211> LENGTH: 675
<212> TYPE: DNA
<213> ORGANISM: Artificial Sequence
<220> FEATURE:
<223> OTHER INFORMATION: Genome of HBc-L2 fusion gene

<400> SEQUENCE: 3
catatggata ttgacccgta caaggaattc ggcgctacag tcgagcttct atcctttctg     60
ccatctgact tctttccgtc ggtacgtgac ctgcttgata cagcatcagc cctgtaccgc    120
gaggcgcttg aaagccctga acactgctct ccacaccata cagcgttacg gcaggctatt    180
ctgtgttggg gagaactcat gacgctagca acttgggtgg tgtcaattt agaagcatcg     240 gctacccaac tttataaaac atgcaaacag gcaggtacat gtccacctga cattataccct   300 aaggttgaag gcaaaactat tgctgatcaa atattacaac tcgaaggtac aggcggacgc    360
actgggtata ttccattggg aacaaggcct cccacagatg aactggaccc cgctagcaga    420
gatttagttg tttcttatgt gaataccaat atgggactta agtttcgcca gctcttatgg    480
ttccatatta gttgcctgac ctttggtaga gaaaccgtga ttgagtatct ggtttccttt    540
ggggtatgga tacgcacgcc gccagcttac cgcccaccta acgctccaat attgtcgacc    600
cttccggaaa ccactgtggt tcgtcgacgc ggaagaagtc ctcgtcgcag gacaccatca    660
ccatgctaag gatcc                                                    675

<210> SEQ ID NO 4
<211> LENGTH: 105
<212> TYPE: DNA
<213> ORGANISM: Human papillomavirus

<400> SEQUENCE: 4
gcatcggcta cccaacttta taaaacatgc aaacaggcag gtacatgtcc acctgacatt     60
atacctaagg ttgaaggcaa aactattgct gatcaaatat acaa                    105

<210> SEQ ID NO 5
<211> LENGTH: 51
<212> TYPE: DNA
<213> ORGANISM: Human papillomavirus

<400> SEQUENCE: 5
ggtacaggcg gacgcactgg gtatattcca ttgggaacaa ggcctcccac a              51

METHOD FOR ENHANCING IMMUNOGENICITY OF EPITOPE PEPTIDE OF HPV ANTIGEN, VIRUS-LIKE PARTICLE, AND METHOD FOR PREPARING HPV VACCINE

CROSS-REFERENCE TO RELATED APPLICATIONS

This application is a continuation-in-part of International Patent Application No. PCT/CN2015/086636 with an international filing date of Aug. 11, 2015, designating the United States, now pending, and further claims foreign priority benefits to Chinese Patent Application No. 201410419379.X filed Aug. 22, 2014. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a method for enhancing immunogenicity of an epitope peptide of an HPV antigen, a virus-like particle, and a method for preparing an HPV vaccine.

Description of the Related Art

Human papillomavirus (HPV) is a genus of virus that can cause genital warts or cancers. HPV genome includes two late transcribed regions for encoding a primary capsid L1 and a secondary capsid L2 respectively. Conventional HPV vaccines are designed based on the L1 antigen and have obvious serum specificity. The HPV L2 also has immunogenicity and L2 possesses cross-neutralizing epitopes. However, the antigen peptide of the neutralizing epitope of the HPV L2 has relatively small molecular weight, and the immunization thereof is insufficient to trigger the immuno-reaction.

SUMMARY OF THE INVENTION

In view of the above-described problems, it is one objective of the invention to provide a method for enhancing immunogenicity of an epitope peptide of an HPV antigen.

It is another objective of the invention to provide a virus-like particle capable of expressing the antigen peptide of HPV acquired by the method for enhancing immunogenicity of the epitope peptide of the HPV antigen.

It is still another objective of the invention to provide a method for preparing a virus-like particle (VLP) comprising antigen peptide of HPV.

It is still another objective of the invention to provide a method for preparing an HPV vaccine by using the virus-like particle.

To achieve the above objective, in accordance with one embodiment of the invention, there is provided a method for enhancing immunogenicity of an epitope peptide of an HPV antigen, the method comprising: assembling a gene of an HPV antigen into a gene of HBc, exogenously expressing a resulting assembled gene to acquire a fusion protein, allowing the fusion protein to automatically assemble to form a virus-like particle comprising the HPV antigen on a surface of the virus-like particle, to obtain HBc-HPV virus-like particle.

In a class of this embodiment, the gene of the HPV antigen is a late transcribed region of HPV encoding a primary capsid protein L1 or a late transcribed region of HPV encoding a secondary capsid protein L2.

In a class of this embodiment, the gene of the HPV antigen is a late transcribed region of HPV encoding a secondary capsid protein L2.

In a class of this embodiment, the HPV antigen presented on the virus-like particle is one antigen peptide of L1 or one antigen peptide of L2, or multiple antigen peptides of L1 or L2, or a couplet of multiple antigen peptides of L1 or L2.

In a class of this embodiment, the HPV antigen presented on the virus-like particle is a couplet of two antigen peptides of L2, and the two antigen peptides of L2 are represented by SEQ ID NO. 1: ASATQLYKTCKQAGTCPPDIIPKVEGK-TIADQILQ, and SEQ ID NO. 2: GTGGRTGYIPLGTRPPT, respectively.

In a class of this embodiment, the antigen peptide of HPV is totally exposed on the surface of the virus-like particle formed by HBc, and the antigen peptide presented on the surface of the virus-like particle of HBc is multiple copies.

In a class of this embodiment, multiple exogeneous genes are inserted into the gene of HBc in the absence of affecting the formation of the virus-like particle of the HBc.

In accordance with another embodiment of the invention, there is provided a virus-like particle capable of expressing the antigen peptide of HPV acquired by the above method, being a HBc-L2 fusion protein, where a genome for encoding the HBc-L2 fusion protein is represented by SEQ ID NO. 3.

In accordance with still another embodiment of the invention, there is provided a method for preparing VLP comprising antigen peptide of HPV, the method comprising soluble expressing the HBc-L2 fusion protein in an expression system of *Escherichia coli* and automatically assembling the HBC-L2 fusion protein into the VLP.

An expression vector of the above virus-like particle is constructed as follows:

1) a cloning vector is transformed to competent cells DH5a, monoclonal is picked and inoculated to a 5 mL LB culture medium, and the cultivation is conducted at a rotational speed of 200 rpm at 37° C. for overnight;

2) plasmid is extracted according to instructions for a plasmid extraction kit, and the extraction effect of the plasmid is identified using 1% agarose gel electrophoresis;

3) a target gene is excised from the cloning vector by double digestion of BamHI and NdeI;

4) the target gene is recovered according to instructions of a gel recovery kit;

5) the recovered target gene and an expression vector plasmid pET 9a after double digestion of BamHI and NdeI are ligated by a ligase at 16° C. for overnight;

6) a resulting ligated product is transformed into BL21 (DE3), monoclonal is picked for performing PCR amplification, positive clones are inoculated to an LB culture medium, and plasmid is extracted for restriction digestion identification; and 7) positive strains are proliferated for preservation.

In 1), the cloning vector is constructed by life technology company, and the target gene (comprising restriction sites of BamHI and NdeI at two ends) is synthesized by an out-sourcing company and is ligated to the T vector to construct the cloning vector.

Preferably, in the method for preparing the virus-like particle, the expression and purification of the HBc-HPV VLP are as follows:

I. Expression of HBc-HPV VLP 1) strain recovery: 10 μL frozen bacteria liquid is inoculated to a 50 mL LB culture medium and cultured at 37° C. in a shaker at a rotational speed of 250 rpm for overnight;

2) strain proliferation: the recovered bacteria liquid is proliferated according that 5 mL recovered bacteria liquid is inoculated to a 100 mL LB culture medium; 1 L LB culture medium is added to a 2 L triangle bottle and cultured at 37° C. under the rotational speed of 250 rpm for overnight until OD600 is equal to 0.6-0.7;

3) induction of expression: IPTG is added to the culture medium to induce the expression of the target protein, in which, the induction was conducted at 25° C. by adding 1 mM IPTG;

4) strain acquisition: after 4 hrs of induction, the induction is finished, and a resulting product is centrifuged at 8000 rpm for 10 min, and bacteria precipitate is collected; and 5) ultrasonic crushing: the bacteria precipitate is resuspended using 400 mL of a TGE buffer (including 50 mM Tris, 0.5 mM EDTA, 50 mM Nacl, 5% glycerine) and then crushed by ultrasonic wave in ice bath, and resulting bacteria are examined under microscope to ensure total crushing thereof.

II. Purification of HBc-HPV VLP:

1) protein collection: after ultrasonic crushing, a resulting mixture is centrifuged at 8000 rpm for 10 min, and a supernatant is collected;

2) protein precipitation: the protein supernatant is gradually added with $(NH_4)_2SO_4$ powder while magnetically stirring to yield a final concentration of the powder to be 10% w/v, and when the powder is fully dissolved, a resulting solution is allowed to stand at 4° C. for 2 hrs;

3) the resulting solution is centrifuged to collect a precipitate, a weight of the precipitate is calculated, and the precipitate is re-suspended using TGE buffer according to a ratio that every 1 g of the precipitate necessitate 60 mL of the buffer;

4) the resuspended solution is re-centrifuged to collect a supernatant, and the supernatant is allowed to pass through a 0.22 μm filter membrane;

5) washing by a film package: a resulting filtrate is filtered by a 100 KDa film package several times for removing proteins of small molecular weight and concentrating a volume of the filtrate, the filtrate is concentrated to a volume of approximately 10 mL after the washing and filtration, and a resulting solution is allowed to pass through a 0.22 μm filter membrane;

6) a concentrated solution is separated and purified by using CL-4B gel, and a first peak is collected; and 7) a purity of the protein and a particle size of the VLP are identified using molecular sieve high performance liquid chromatography (SEC-HPLC) and multi-angle laser light scattering (MALS).

In accordance with still another objective of the invention, there is provided a method for preparing an HPV vaccine by using the above virus-like particle.

In a class of this embodiment, the method for preparing the HPV liquid injection vaccine not containing any adjuvant or protectant by using the virus-like particle is as follows:

1) replacement of buffer solution: a buffer solution of a vaccine solution is replaced by 20 mg/mL NaCl, or 4 mM PB, or 8 mg/mL NaCl+2 mM PB 2) a protein concentration is measured according to instructions of the protein concentration measuring kit;

3) corresponding buffer solution is replenished until an antigen concentration is 100 μg/mL or 50 μg/mL;

4) a resulting solution is filtered in sterilized condition to yield a semi-product of vaccine;

5) the semi-product of the vaccine is dispensed by an automatic dispenser, and each preparation contains 0.5 mL vaccine; and 6) sealing: when the vaccine is stored in an ampoule bottle, the ampoule bottle is required to be sealed, and when the vaccine is stored in a penicillin bottle, the penicillin bottle is required to sealed by pressing a cover.

In a class of this embodiment, a final product of the vaccine is added with an aluminum hydroxide adjuvant, which is specifically conducted as follows:

1) replacement of buffer solution: a buffer solution of a vaccine solution is replaced by 20 mg/mL NaCl, or 4 mM PB, or 8 mg/mL NaCl+2 mM PB 2) a protein concentration is measured according to instructions of the protein concentration measuring kit;

3) corresponding buffer solution is replenished until an antigen concentration is 900 μg/mL or 450 μg/mL;

4) a resulting solution is filtered in sterilized condition to yield a semi-product of vaccine;

5) 1% aluminum hydroxide adjuvant is added to the semi-product of the vaccine, the corresponding buffer solution is replenished to yield a final concentration of the adjuvant to be <0.1%, and a final concentration of the protein antigen to be 100 μg/mL or 50 μg/mL;

6) the semi-product of the vaccine is dispensed by an automatic dispenser, and each preparation contains 0.5 mL vaccine;

7) sealing: when the vaccine is stored in an ampoule bottle, the ampoule bottle is required to be sealed, and when the vaccine is stored in a penicillin bottle, the penicillin bottle is required to sealed by pressing a cover; and 8) bottles containing the vaccine are labelled and preserved at 4° C.

Advantages of the method for enhancing immunogenicity of an epitope peptide of an HPV antigen, the virus-like particle, and the method for preparing the HPV vaccine according to embodiments of the invention are summarized as follows: the method for enhancing immunogenicity of the epitope peptide of the HPV antigen of the invention overcomes the shortages including the poor immunogenicity of the antigen peptide and the influence of the inserted sequence on the VLP assembly of the HBc in the prior art. The inserting site for the L2 antigen peptide in the HBc is appropriately designed so that at least one copies of the L2 antigen peptide are covered on the surface of the HBc-VLP, that is, the system of the invention is able to present at least one copies of the L2 antigen peptide on the surface of the pseudovirus to make the neutralizing epitopes of HPV L2 totally represented on the surface of the HBc pseudovirus particles, thus effectively enhancing the immunogenicity of the neutralizing epitopes of the L2. The obtained HBc-L2 fusion proteins are automatically assembled into the VLP after soluble expression, so that the complicate processes including denaturation and renaturation of the in vitro protein in order to form the VLP are deleted, and the recovery rate of the antigen VLP is greatly improved. The obtained HBc-L2 fusion protein possesses great application prospect in production of the vaccine for preventing HPV infection.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a method for enhancing immunogenicity of an epitope peptide of an HPV antigen, a virus-like particle, a method for preparing the virus-like particle, and a method for preparing an HPV vaccine are described below. It should be noted that the following examples are intended to describe and not to limit the invention.

EXAMPLE 1

Construction of Hbc-L2 VLP Recombinant Fusion Protein

1) Synthesize of HBc-L2 Gene Sequence

HBc-L2 fusion gene (comprising restriction sites of BamHI and NdeI at two ends) was synthesized by Life technology company, the fusion gene was then ligated to a T vector. Information of the fusion gene is listed in Table 1:

TABLE 1

| Gene information concerning fusion protein | |
|---|---|
| Complete genome | catatggatattgacccgtacaaggaattcggcgctacagtcgagcttctatcctttctgccatctgac ttctttccgtcggtacgtgacctgcttgatacagcatcagccctgtaccgcgaggcgcttgaaagccct gaacactgctctccacaccatacagcgttacggcaggctattctgtgttggggagaactcatgacgcta gcaacttgggtgggtgtcaatttagaagcatcggctacccaactttataaaacatgcaaacaggcaggt acatgtccacctgacattatacctaaggttgaaggcaaaactattgctgatcaaatattacaactcgaa ggtacaggcggacgcactgggtatattccattgggaacaaggcctcccacagatgaactggacccgct agcagagatttagagtacttatgtgaataccaatatgggacttaagatcgccagctcttatggttccat attagagcctgacctaggtagagaaaccgtgattgagtatctggtacctaggggtatggatacgcacgc cgccagcttaccgcccacctaacgctccaatattgtcgaccatccggaaaccactgtggttcgtcgacg cggaagaagtcctcgtcgcaggacaccatcacca tgctaaggatcc (SEQ ID NO. 3) |
| Genomes of target antigens | gcatcggctacccaactttataaaacatgcaaacaggcaggtacatgtccacctgacattatacctaag gttgaaggcaaaactattgctgatcaaatattacaa (SEQ ID NO. 4) ggtacaggcggacgcactgggtatattccattgggaacaaggcctcccaca (SEQ ID NO. 5) |
| LE linker1 | ttagaa |
| LE linker2 | ctcgaa |
| DEL linker | gatgaactg |
| Restriction site of NdeI | catatg |
| Restriction site of BamHI | ggatcc |

2) Induced Expression of HBc-VLP

Figure 1:
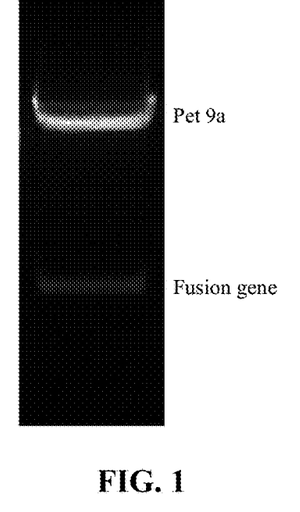
FIG. 1 is a restriction map of HBc-L2-pET 9a expression vector, in which, a DNA fragment having a size of 670 bp is obtained from the restriction digestion and is coincident with a theoretical size of a fusion gene.

The target gene was recovered from the T vector by double digestion of BamHI and NdeI, then ligated to pET 9a expression vector, and a recombinant vector was transformed into BL21 (DE3), as shown in FIG. 1, the transformation was demonstrated to be success by restriction digestion and PCR verification.

3) IPTG-Induced Expression

Figure 2:
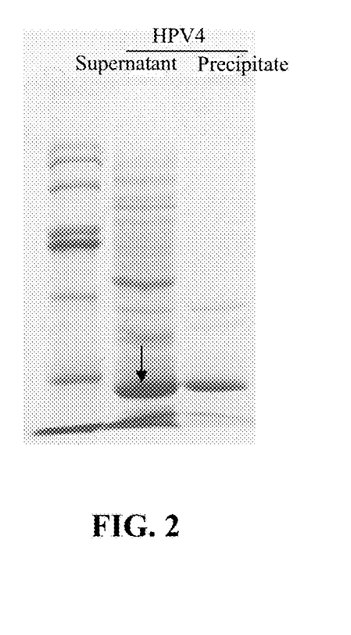
FIG. 2 illustrates identification of induced expression of HBc-L2, in which, after the IPTG-induced expression, a bacteria precipitate is collected after centrifuge and then ultrasonically crushed to collect a supernatant and a precipitate, it is known from electrophoresis results of the supernatant and the precipitate that the target protein is predominant in the supernatant, which indicates that the constructed fusion gene expresses the target protein in the form of soluble expression.

10 μL frozen bacteria liquid was inoculated to a 50 mL LB culture medium for overnight to revive the strain. At the second morning, the revived bacteria liquid was proliferated according that 5 mL revived bacteria liquid was inoculated to a 100 mL LB culture medium. When OD600 was equal to 0.6-0.7; 1 mM IPTG was added to induce expression at an induction temperature of 25° C. After 4 hrs induction, a resulting product was centrifuged to collect a bacteria precipitate. The bacteria precipitate was thereafter ultrasonically crushed, and a resulting supernatant and a resulting precipitate were respectively analyzed by SDS-PAGE electrophoresis, results of which were shown in FIG. 2, and the constructed expression vector primarily adopts the soluble expression to express the target protein.

It should be noted that the gene synthesis, the construction of the expression vector, the induced expression, the ultrasonic crush, and the SDS-PAGE analyses in this example are all common experiment methods in the technical field and relating experiment skills are well known by the persons skilled in the art. The culture medium used in the whole induced expression process is the common LB culture medium.

Furthermore, the electrophoresis picture provided in this example is only intended to explore whether the expression vector adopts the soluble expression and but does not indicate the real expression amount of this example. After optimization of the culture medium and the adjustment of the fermentation process, the expression amount is multiple times of that indicated in the electrophoresis picture.

EXAMPLE 2

Identification of VLP of HBc-L2 Recombinant Antigen Fusion Protein

Bacteria after fermentation were collected, crushed by ultrasonic wave, and centrifuged to collect a supernatant. The supernatant was then performed with crude purification. The crude purified sample was analyzed by SEC-HPLC and MALS and results indicated that particles of large molecular weight exist in the supernatant. The crude purified sample then identified by electron microscope to demonstrate the existence of the VLP particles.

Crude Purification and Ddentification of VLP of HBc-L2 Recombinant Protein

1) After the fermentation, the bacteria were collected by centrifuge and resuspended by using 400 mL of a TGE buffer (including 50 mM Tris, 0.5 mM EDTA, 50 mM Nacl, 5% glycerine) and then crushed by ultrasonic wave in ice bath.

2) A supernatant was collected and gradually added with $(NH_4)_2SO_4$ powder while magnetically stirring. When the powder was fully dissolved, a resulting solution was allowed to stand at 4° C. for 2 hrs.

3) The resulting solution was centrifuged to collect a precipitate, a weight of the precipitate was calculated, and the precipitate is re-suspended and dissolved using buffer according to a ratio that every 1 g of the precipitate necessitated 60 mL of the buffer.

4) The resuspended solution was centrifuged to collect a supernatant, and the supernatant was filtered by a 0.22 μm filter membrane and then ultra-filtered by a 100 KDa film package.

Figure 3:
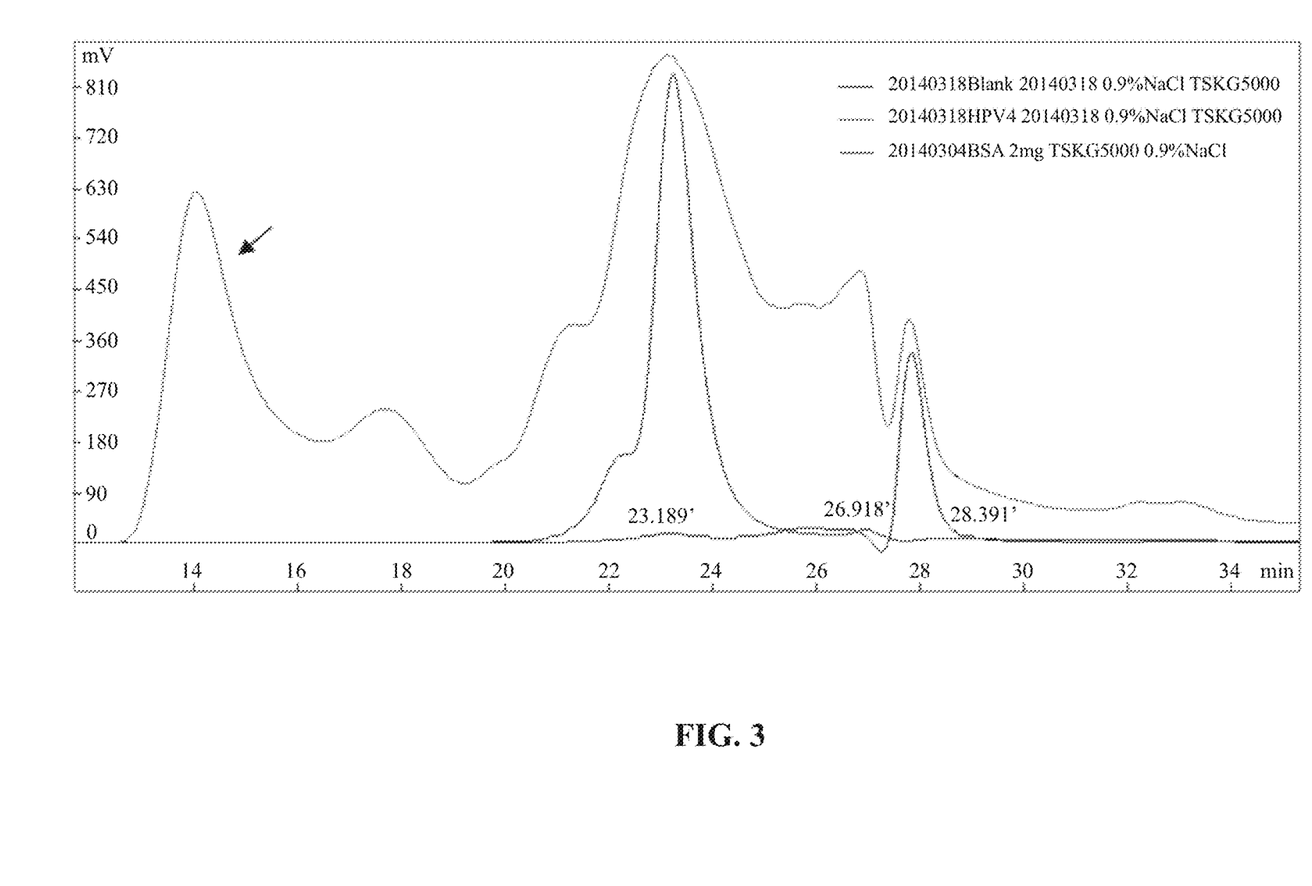
FIG. 3 is identification chart of HBC-L2 VLP using HPLC, and it is indicated from the chart that the designed HPV L2 fusion peptide only contains 52 amino acids and has a theoretical molecular weight of approximately 22 KD, however, the SEC-HPLC analysis (using TSK G5000) shows that the acquired purified product has a molecular weight (retention time of 14 min) being much larger than that of the BSA protein (molecular weight of 66 KD, and retention time of approximately 23 min), which indicates that the fusion protein automatically assembled into the VLP particles.
Figure 4:
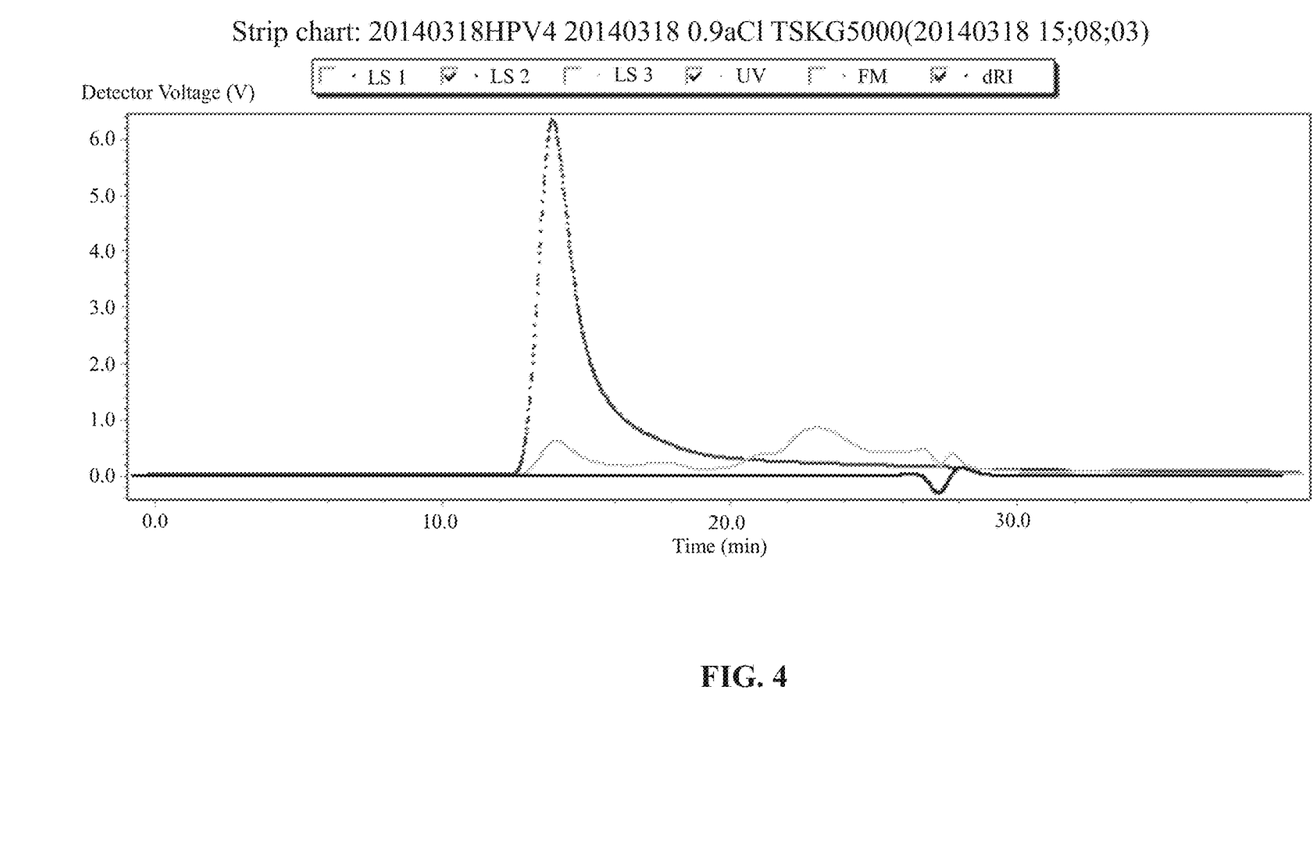
FIG. 4 is identification chart of HBC-L2 VLP using MALS, it is known combining the results of SEC-HPLC and MALS that the expressed product exists with large molecular particles having good uniformity in the molecular weight.
Figure 5:
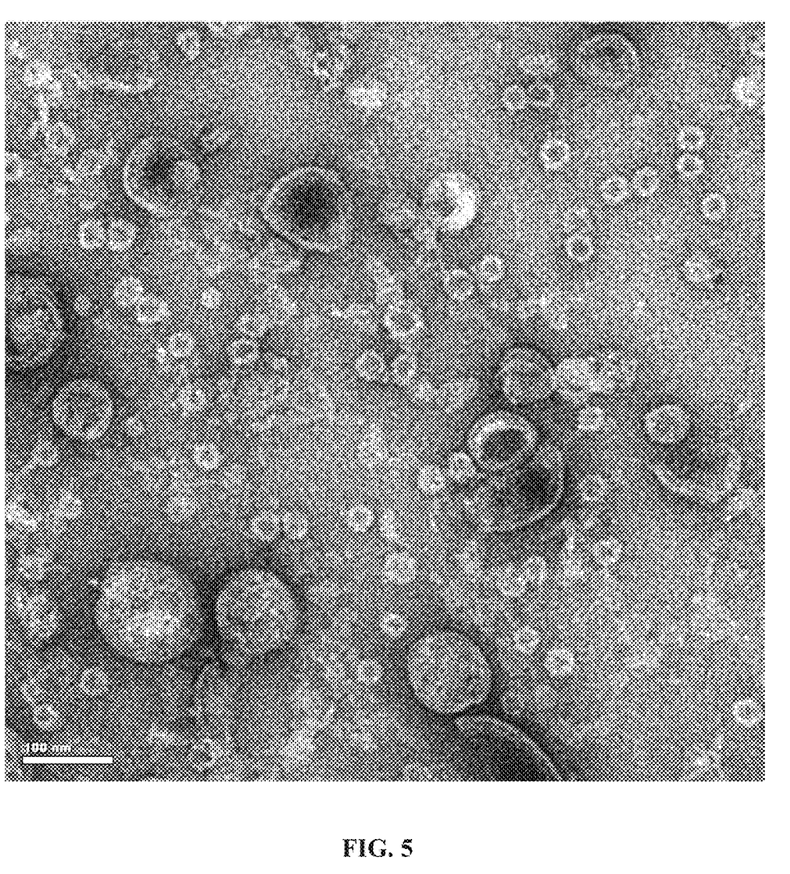
FIG. 5 is electron microscope picture of HBc-L2 VLP, which directly shows the success automatic assembly of the VLP from the fusion protein, coincident with the results of SEC-HPLC and MALS; in addition, it is known from the electron microscope picture that the efficiency of the automatic assembly into the VLP particle from the fusion protein is high, and the uniformity of the VLP particle is good.

5) VLP particles were identified, and a concentrated solution was detected by SEC-HPLC and MALS, it was known from the results in FIGS. 3-4 that particles of large molecular weight existed, and the particles of the large molecular weight was ensured to have the VLP structure, as shown in FIG. 5, by electron microscope identification.

EXAMPLE 3

Purification of VLP of HBc-L2 Recombinant Antigen Fusion Protein

To further improve the method for purifying the HBc-L2 VLP antigen on the basis of Example 2, the concentrated solution after ultra-filtration by the 100 KDa film package was allowed to pass through a molecular sieve and then purified by the CL-4B gel or sepharose-4FF gel. A purity of the target antigen VLP was at least 80 wt. %. Such purification process is characterized in simple process, high recovery rate, and easy magnification. Specifically, the purification process of VLP was carried out as follows:

1) Protein collection: after ultrasonic crushing, a resulting mixture was centrifuged at 8000 rpm for 10 min, and a supernatant was collected.

2) Protein precipitation: the protein supernatant was gradually added with $(NH_4)_2SO_4$ powder while magnetically stirring to yield a final concentration of the powder to be 10% w/v, and when the powder is fully dissolved, a resulting solution was allowed to stand at 4° C. for 2 hrs.

3) The resulting solution was centrifuged to collect a precipitate, a weight of the precipitate was calculated, and the precipitate was re-suspended using TGE buffer according to a ratio that every 1 g of the precipitate necessitated 60 mL of the buffer.

4) The resuspended solution was re-centrifuged to collect a supernatant, and the supernatant was allowed to pass through a 0.22 μm filter membrane.

5) Washing by the film package: a resulting filtrate was filtered by the 100 KDa film package for several times for removing proteins of small molecular weight and concentrating a volume of the filtrate, the filtrate was concentrated to a volume of approximately 10 mL after the washing and filtration.

6) A concentrated solution was separated and purified by using CL-4B gel or sepharose 4FF gel, and a first peak was collected.

Figure 6:
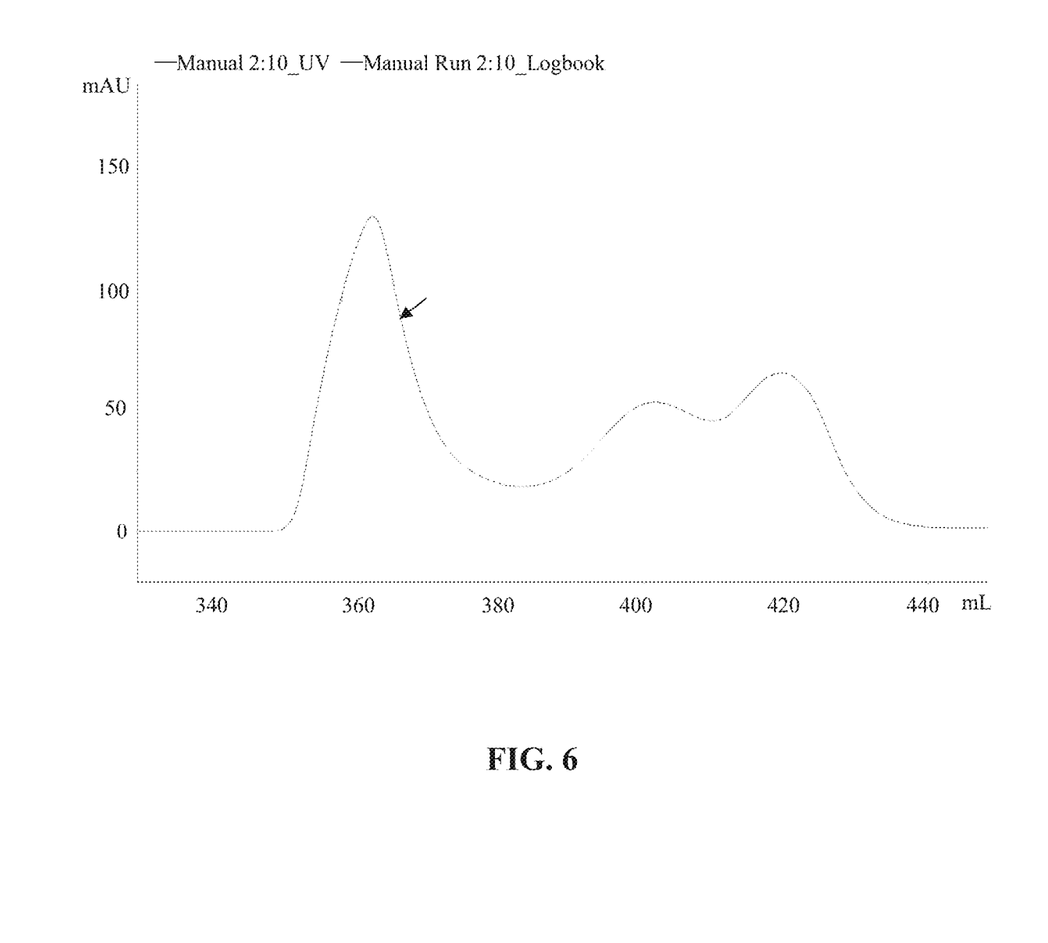
FIG. 6 is a purification chart of 100 KDa ultra-filtrate separated by a CL-4B gel, in which, the 100 KDa ultra-filtrate concentrated solution is effectively separated by the CL-4B to yield VLP, and a peak indicated by an arrow is the VLP particles of fusion protein separated by the CL-4B.
Figure 7:
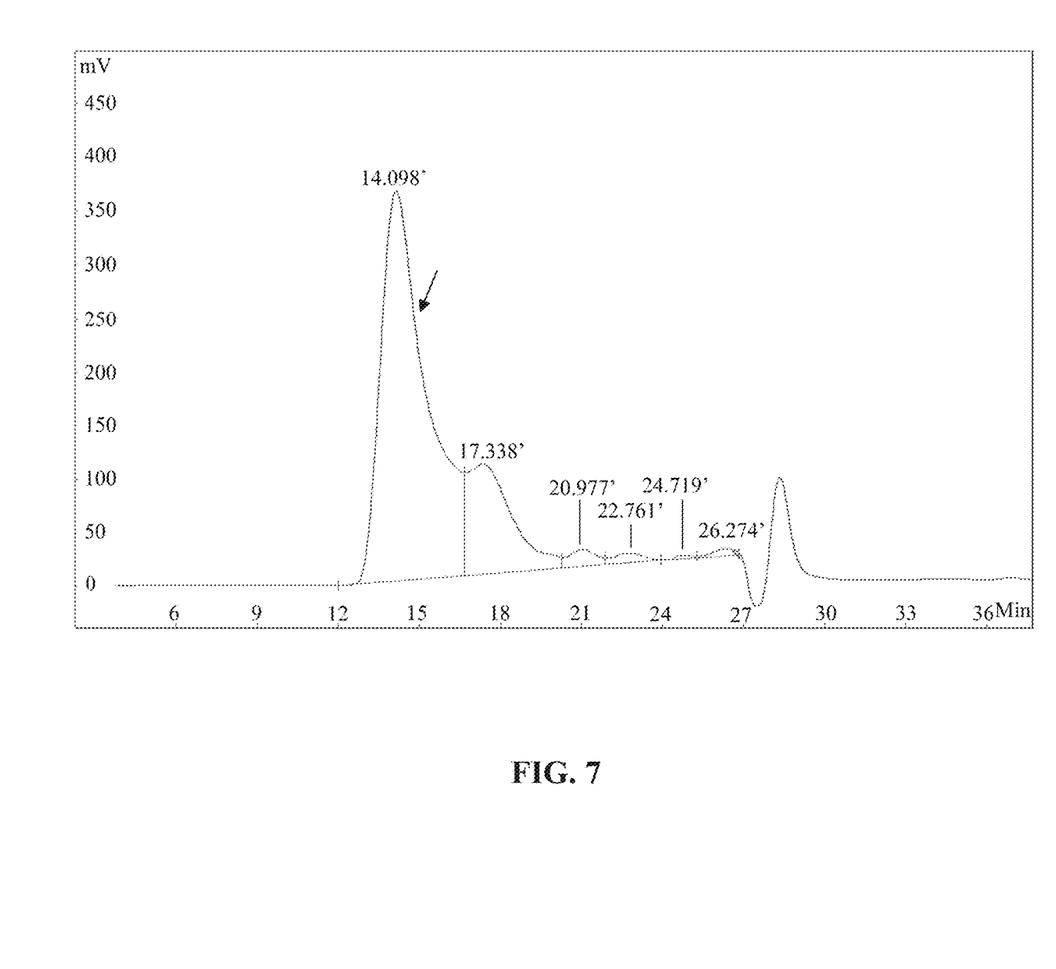
FIG. 7 is purity analysis of HBc-L2 VLP particles (using HPLC), in which, the purity analysis of the purified VLP antigen using SEC-HPLC is shown, and a target peak indicated by an arrow has a purity of 85 wt. %.

7) The purity of the protein was identified by SEC-HPLC and MALS, the ultra-filtrate by the 100 KDa film package was allowed to pass through the molecular sieve to collect a filtrate by tubes. The molecular weight and the purity of the protein were analyzed by SEC-HPLC, results indicated that the large molecular particles were predominant in the first peak, and the purity exceeded 80 wt. %, as shown in FIGS. 6-7. Analysis conditions were listed in Table 2.

TABLE 2

| Number | Retention time | Concentration | Peak area |
|---|---|---|---|
| 1 | 14.098 | 85.84 | 48950851 |
| 2 | 17.338 | 9.98 | 5694013 |
| 3 | 20.977 | 1.974 | 1125395 |
| 4 | 22.761 | 1.296 | 739311 |
| 5 | 24.719 | 0.2581 | 147157 |
| 6 | 26.274 | 0.6428 | 366527 |
| Total | | 100 | 26.274 |

EXAMPLE 4

HBc-L2 VLP Vaccine Preparation

A volume of the vaccine was designed to be 0.5 mL, and each preparation contains 25 μg or 50 μg of VLP protein, adjuvant was optionally added in the preparation. When the adjuvant was added, the aluminum hydroxide adjuvant was adopted, and a buffer solution of the preparation was NaCl or NaCl added with PB, as listed in Table 3 and Table 4.

TABLE 3

HBc-L2 VLP vaccine preparation (first dosage)

| | Preparation 1 | Preparation 2 | Preparation 3 | Preparation 4 | Preparation 5 | Preparation 6 |
|---|---|---|---|---|---|---|
| VLP content | 25 μg | 25 μg | 25 μg | 25 μg | 25 μg | 25 μg |
| NaCl | 10 mg | 10 mg | | | 4 mg | 4 mg |
| PB | | | 4 mM | 4 mM | 2 mM | 2 mM |
| Aluminum hydroxide adjuvant | | 500 μg | | 500 μg | | 500 μg |
| Vaccine volume | 0.5 mL | | | | | |
| pH value | 5.5-7.5 | | | | | |

TABLE 4

HBc-L2 VLP vaccine preparation (second dosage)

| | Preparation 1 | Preparation 2 | Preparation 3 | Preparation 4 | Preparation 5 | Preparation 6 |
|---|---|---|---|---|---|---|
| VLP content | 50 μg | 50 μg | 50 μg | 50 μg | 50 μg | 50 μg |
| NaCl | 10 mg | 10 mg | | | 4 mg | 4 mg |
| PB | | | 4 mM | 4 mM | 2 mM | 2 mM |
| Aluminum hydroxide adjuvant | | 500 μg | | 500 μg | | 500 μg |
| Vaccine volume | 0.5 mL | | | | | |
| pH value | 5.5-7.5 | | | | | |

EXAMPLE 5

Immunization of Mice by HBc-L2 VLP Antigen

The HBc-L2 VLP antigen having an antigen purity of at least 80 wt. % was prepared to immunize mice. To compare the enhanced effect of the immunogenicity of the peptide after being effectively packed into VLP by the HBc, a single L2 antigen peptide carried with a GST tag was constructed, and the GST-L2 was utilized as a contrast group to study the VLP immunogenicity. The immunization schemes of the mice designed in the experiment were listed in Table 5.

TABLE 5

Experiment scheme for study the immunogenicity of the VLP antigen

| Experiment groups | HBc-L2 VLP | GST-L2 | Blank control |
|---|---|---|---|
| Dose | containing adjuvant (μg) | Not containing adjuvant (μg) | Not containing adjuvant |
| | 20  5  1 | 20  5  1 | 20  5  1 | Adjuvant NS |
| Animal number | 10 animals for each group | | |
| Immune process | Immunized for three times, an immunization interval being two weeks | | |
| Immune method | | | |

The serum samples after the second immunization and the third immunization were collected, and the serum tilters of the mice were detected by ELISA. The ELISA is the common experiment means. The experiment adopted the HPV-L2 antigen peptide as the coating antigen to detect the tilters of the anti-L2 IgG antibody in the serum samples of mice, in which, the coating concentration was 5 μg/mL or 100 μL/well, the coating condition was 4° C. for overnight. The ELISA plate was blocked by 2% BSA with a concentration of 200 μL/well. When detecting the serum, the last time for the serum and the secondary antibody incubation were 1 hr, and each time after the incubation, the ELISA plate was washed by 0.1% PBST for 5 times, and TMB was added after the secondary antibody incubation, and experiment results were measured by $OD_{450}$ and listed in Table 6.

TABLE 6

Experiment results of immunogenicity of VLP antigen

| Immunizing antigen | Adjuvant | immune dose (μg) | Serum tilter after second immunization | Serum tilter after third immunization |
|---|---|---|---|---|
| GST-L2 | Not containing adjuvant | 20 | 50 | 100 |
| | | 10 | <50 | 50 |
| | | 5 | <50 | <50 |
| HBc-L2 | Not | 20 | $2 \times 10^4$ | $8 \times 10^5$ |

TABLE 6-continued

Experiment results of immunogenicity of VLP antigen

| Immunizing antigen | Adjuvant | immune dose (μg) | Serum tilter after second immunization | Serum tilter after third immunization |
|---|---|---|---|---|
| VLP | containing adjuvant | 10 | $9.1 \times 10^3$ | $3 \times 10^4$ |
| | | 5 | $1.2 \times 10^2$ | $5 \times 10^3$ |
| | Containing adjuvant | 20 | $1 \times 10^5$ | $5.8 \times 10^6$ |
| | | 10 | $4 \times 10^4$ | $9 \times 10^5$ |
| | | 5 | $3.6 \times 10^3$ | $5.8 \times 10^4$ |

It was indicated from the immunogenicity of the HBc-L2 VLP that the immunization effect of the HBc-L2 VLP was much better than the single GST-L2 antigen peptide. When the mice were immunized by HBc-L2 VLP, the immunization effect after the third immunization was better than that after the second immunization, thus, the HBc-L2 VLP enhanced the immunization effect. In addition, the aluminum adjuvant was able to obviously improve the immunoreaction of the antigen. And the results of the animal experiments proved that the VLP particles formed from the L2 antigen peptide by recombinant construction of the HBC-L2 was able to stimulate the organism to produce obvious immunoreaction, and the stimulated antibody level provided strong enough protection.

EXAMPLE 6

Protection Experiment

The HPV-specific neutralizing antibodies in the mice serum were measured using the HPV pseudovirus neutralization experiment to study the protection performance of the vaccine.

293FT cells were utilized as host cells for the neutralization experiment, and specific operations for the experiment were as follows:

1) 293FT cells in a cell vival was digested by trypsin to regulate the cell concentration to be $1.5 \times 10^5$/mL, then the cells were added to a 96-well plate with each well added with 100 μL of the cells and cultured at 37° C. in a 5% $CO_2$ incubator for 4 hrs.

2) The serum to be tested was diluted by series gradient dilution, and the pseudovirus was diluted according to pre-determined folds.

3) The serum and the pseudovirus particles were mixed according to the ratio of 1:1, volumes of the serum and the pseudovirus particles were respectively 50 μL, and neutralization was conducted at 4° C. for 2 hrs.

4) The neutralized solution was added to the 96-well plate and cultivated at 37° C. in the 5% $CO_2$ incubator for 72 hrs.

5) Results were observed under a fluorescence microscope, wells having an infection inhibition rate of exceeding 50% were defined as positive wells, and experiment results were recorded in Table 7.

TABLE 7

Experiment results of neutralizing antibody in HPV vaccine immunized-mice

| Immunizing antigen | Adjuvant | Immune dose (μg) | Neutralization titration with HPV16 pseudovirus | Neutralization titration with HPV18 pseudovirus |
|---|---|---|---|---|
| GST-L2 | Not containing adjuvant | 20 | | |
| | | 10 | | |
| | | 5 | | |
| HBc-L2 VLP | Not containing adjuvant | 20 | 100 | 150 |
| | | 10 | 50 | 25 |
| | | 5 | | 12.5 |
| | Containing adjuvant | 20 | 150 | 150 |
| | | 10 | 100 | 75 |
| | | 5 | 50 | 25 |

It was proved from the results that neutralizing antibody was not detected in the GST-L2 antigen peptide immunized serum, which was possibly because that the GST-L2 antigen peptide was difficult to stimulate effective immunoreaction.

Although the L2 antigen peptide designed in the experiment was derived from HPV16, it was indicated that the antigen epitope peptide possessed cross-neutralizing activity, which was able to effectively neutralizing HPV16 pseudovirus as well as HPV18 pseudovirus.

Figure 8:
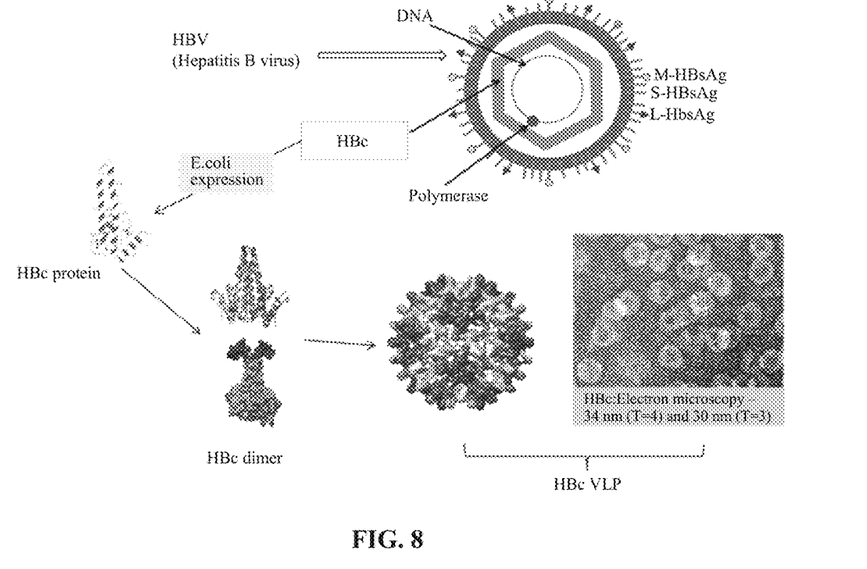
FIG. 8 is a picture showing assembly of an HBc protein of an HBV into a VLP, in which, the HBc protein of HBV after being expressed in *E. coli* is automatically assembled into the VLP particles.
Figure 9:
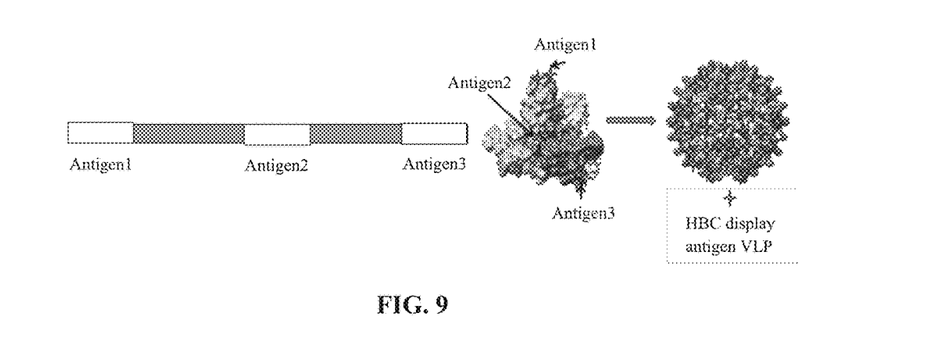
FIG. 9 is simulated image of design of an HBc-L2 VLP vaccine, in which, a front section, a middle section, and a rear section of the HBc can be inserted with exogeneous antigen without affecting the formation of the VLP, and more importantly, after being assembled into the VLP via the HBc protein, the inserted antigens are all presented on a surface of the assembled VLP.

Design principle of the invention and the benefits thereof are analyzed hereinbelow:

The design principle of the general vaccine HBc-L2 VLP is as shown in FIG. 8, the HBc protein of the HBV can be automatically assembled into the VLP particles after being expressed in the *E. coli*. During the process, a front section, a rear section, and a middle section of the HBc protein can be introduced with exogenous antigens in the absence of affecting the formation of the VLP. What is more important, as shown in FIG. 9, the inserted antigens are all exposed on the surface of the HBc VLP. Thus, the expression of the HBc-L2 VLP based on the characteristics of the formation of VLP by expression of exogenous antigens of HBc, the immunogenicity of the L2 antigen peptide is effectively improved. In addition, the insertion of the L2 gene does not affect the formation of the HBc VLP, and the inserted epitope peptides of the antigen re optionally the same one or different, or a fusion gene of two epitopes.

In Example 1, the fusion protein includes a connector LE disposed between the vaccine vector and the neutralizing epitope of HPV L2. The addition of such flexible connector is able to avoid mutual affects between the antigen protein and the HBc in the formation of the VLP, which is beneficial to the formation of the correct conformation. In addition, the insertion site for the exogenous gene in the HBc is not just unique, and such insertion sites can be inserted with the same peptides or with different peptides. The exogenous gene is optionally inserted into the front section, the middle section, or the rear section of the HBc, and the insertion does not affect the formation of the HBc VLP. The exogenous gene inserted into the HBc is optionally one neutralizing epitope or two neutralizing epitopes, at one insertion site or at different insertion sites, or the two neutralizing epitopes are fusion expressed at the same site.

It is known from the above examples that the design of the neutralizing epitope peptide of HPV L2 enables the HBc-L2 VLP antigen to possess a broad-spectrum anti-virus capacity, thus broadening the serotype restrictions on the L1 vaccine. The particle of the prepared HBc-L2 VLP is uniform and consistent in batches. The provided method for purifying the VLP antigen has simple process and is able to acquire antigens having a VLP purity of exceeding 80%. After the mice are immunized with the prepared HBc-L2 VLP antigen, the antigen reaction having a titer much higher than L2 is acquired.

To better understand the technical scheme of the invention, the following problems need to be illustrated:

1) A potential HPV vaccine that has much broader prevention spectrum is provided in the invention.

The current HPV vaccines on the market are designed typically for the L1 antigen and possess obvious serum specificity. While the HPV16/18 bivalent vaccine can only inhibit approximately 70% HPV infection. To make the vaccine have broader prevention spectrum, HPV multivalent vaccines including more serotypes are required to be designed, for example, the quaternary vaccine developed by the Merck company and the nine-valent vaccine which just passed through the clinical trial. It has been found from the study that the L2 exists with multiple cross-neutralizing epitopes, the single or combination cross-neutralizing epitopes are able to prevent the HPV virus of more serotypes. The antigen peptide possessing much broader cross-neutralizing epitopes are selected as the target gene, and the acquired HBc-L2 VLP enables to neutralize the HVP virus of multiple serotypes, thus being an HPV vaccine possessing broader prevention spectrum.

2) Experimental method for enhancing the immunity using antigen peptide is provided in the invention.

The antigen peptide of the neutralizing epitope of the HPV L2 has very small molecular weight, and the immunization alone is very difficult to stimulate the organism to produce enough strong immunoreaction. This is the reason that the HPV L2 vaccine has been slowly developed although a large quantity of papers have reported that the HPV L2 is able to produce the neutralizing antibody and L2 possesses cross-neutralizing epitopes. By the HBc-VLP antigen-presenting vector, the designed HBC-L2 VLP antigen enlarges the molecular weight and the space configuration of the antigen, which effectively stimulates the immunoreaction of the organism, moreover, the based on the design of the insertion sites in the above examples, the surface of the HBc VLP is covered by the HPV L2 antigen peptides.

In the above examples of the invention, a large amount of copies of the antigen peptide of the L2 cross-neutralizing epitope exist on the surface of the HBc VLP, and the structure of the HBc VLP ensures that the active sites of the antigen peptide of the L2 cross-neutralizing epitope totally exposed outside, therefore stimulate the organisms of the HBc-L2 VLP immunized mice to produce good immunoreactions.

3) The yield of the HBc-L2 VLP of the examples of the invention is greatly improved.

Although the HPV L1 can be automatically assembled into VLP after in vitro expression, the yield of the pseudovirus particle based on the automatic assembly of the L1 antigen is very low. The capsid of HPV is an icosahedron structure formed by 72 L1 protein pentamers, and the in vitro expressed L1 protein need processes of formation of pentamers by five L1 monomers and formation of icosahedron by 72 pentamers in order to assemble the pseudovirus particles which is similar to the HPV virus, but only a small part of the automatically assembled VLP has the icosahedron structure. The yield of the VLP is greatly improved by presenting the L2 antigen peptide via the HBc VLP, thus, the production cost of the HPV vaccine is expected to be greatly decreased 4) The insertion of the L2 neutralizing epitope gene sequence does not affect the assembling efficiency of the HBc VLP.

Many reports have been disclosed on the research of the HBc-VLP as an antigen presenting vector, but as limited by the possible influence of the inserted sequence on the formation of the HBc VLP, the designed vaccine products based on the vector are few. The embodiments of the invention are based on a large quantity of prior studies of molecular biology and structure biology, the insertion site in the HBc is optimized to ensure that the insertion of the L2 bases does not affect the formation of the VLP.

After the soluble expression of the fusion protein in the *E. coli*, VLP is automatically assembled, and the assembly efficiency of the VLP is not lower than the yield of the single HBc VLP. And it is known from the electron microscopy analysis that the uniformity of the size of the VLP is good.

5) The insertion sites for the L2 antigen neutralizing epitope in the HBc have many types.

The insertion sites of L2 in the HBc are optionally disposed in the front section, the middle section, or the rear section of the HBc protein. The epitope peptide of the L2 antigen is inserted into one site or synchronously inserted into two or three sites; optionally, one or two neutralizing epitope of the antigen is inserted. Besides, the insertion sites of the epitope peptide of two fusion antigens are optionally the same site or different sites. Based on the research concept of the embodiment, similar products can be developed. Furthermore, the method for enhancing the antigen peptide provided in the embodiments can also be applied to enhance the immunogenicity of the antigen peptide including the L2 neutralizing epitope.

In summary, the nano-sized heptatitis B core antigen VLP (HBc-VLP) particles are prone to be swallowed by the antigen-presenting cells. The HBc-VLP is an effective antigen vector, and the antigen presented on the HBc-VLP is able to delete the demands for the adjuvants and to produce Th1 immunoreactions. The HBc-VLP is non-infectious, what is different from other VLP, the HBc-VLP does not involved in the interactions of the viral receptors or neutralize the antibody target, thus the vector inhibition is not the primary challenge. The application of the HBc-VLP as the vaccine delivery system can effectively overcome the shortcomings that the polypeptide sequence of small molecular weight cannot effectively stimulate the immune system.

The neutralizing epitope of HPV L2 is inserted into the HBc, and fusion protein is expressed in vitro, thus, during the formation of HBc VLP, the target antigen is presented on the surface of the pseudovirus particles to form the VLP particle having HPV L2 neutralizing epitope covered on the surface thereof, thus enhancing the immunoreaction.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for enhancing immunogenicity of an human papillomavirus (HPV) L2 antigen, the method comprising: constructing a chimeric gene wherein a nucleotide sequence encoding the HPV L2 antigen is inserted into a hepatitis B virus core protein (HBc), gene sequence, expressing the resulting chimeric gene in vitro to acquire a HBc-HPV L2 fusion protein, allowing the fusion protein to automatically assemble to form a virus-like particle comprising the HPV L2 antigen on surface of the virus-like particle, and obtaining the virus-like particle, wherein the HBc-HPV L2 fusion protein is encoded by a nucleotide sequence comprising SEQ ID NO: 3.

2. A virus-like particle comprising a chimeric HBc-HPV L2 fusion protein encoded by a nucleotide sequence comprising SEQ ID NO: 3.

3. The virus-like particle of claim 2, wherein the HBc-HPV L2 fusion protein is capable of being expressed in a soluble form in an expression system of *Escherichia coli* and forming the virus-like particle through self-assembly.

4. A method for preparing an HPV vaccine comprising the virus-like particle of claim 2, wherein the method comprising steps of: expressing the HBc-HPV L2 fusion protein in *Escherichia coli*, forming the virus-like particle through self-assembly, purifying the virus-like particle, and optionally adding adjuvant in the virus-like particle preparation.

* * * * *